United States Patent [19]

Lewis et al.

[11] Patent Number: 5,697,367
[45] Date of Patent: Dec. 16, 1997

[54] SPECIALLY GROUNDED SENSOR FOR CLINICAL SPECTROPHOTOMETRIC PROCEDURES

[75] Inventors: Gary D. Lewis, Grosse Pointe Farms; Oleg Gonopolskiy, Southfield; Wayne P. Messing, Troy; Richard S. Scheuing, Ann Arbor, all of Mich.

[73] Assignee: Somanetics Corporation, Troy, Mich.

[21] Appl. No.: 324,120

[22] Filed: Oct. 14, 1994

[51] Int. Cl.[6] .................................................. A61B 5/00
[52] U.S. Cl. .................................................. 128/633
[58] Field of Search .................. 128/633, 664–667, 128/639, 640, 901

[56] References Cited

U.S. PATENT DOCUMENTS

| | | | |
|---|---|---|---|
| 2,790,438 | 4/1957 | Taplin et al. | 128/633 |
| 3,230,951 | 1/1966 | Teschner | 128/666 |
| 3,602,213 | 8/1971 | Howell et al. | 128/633 |
| 3,769,974 | 11/1973 | Smart et al. | |
| 3,810,460 | 5/1974 | Van Nie | 128/666 |
| 3,814,081 | 6/1974 | Mori | 128/2 L |
| 3,822,695 | 7/1974 | Takayama | 128/2 L |
| 3,910,701 | 10/1975 | Henderson et al. | 128/625 |

(List continued on next page.)

FOREIGN PATENT DOCUMENTS

| | | | |
|---|---|---|---|
| 646376 | 4/1993 | Australia | 128/633 |
| 2517129 | 6/1976 | Germany | 356/32 |
| 2076963 | 12/1981 | United Kingdom . | |
| WO8909566 | 10/1989 | WIPO . | |
| 9412096 | 6/1994 | WIPO | 128/633 |

*Primary Examiner*—Lee S. Cohen
*Attorney, Agent, or Firm*—Price, Heneveld, Cooper, DeWitt & Litton

[57] ABSTRACT

A specially grounded sensor for improving signal-to-noise ratios in clinical spectrometric procedures includes a sensor body carrying electrically actuated spectrometric signal-producing and receiving components, e.g., electro-optical components, for transmittal and reception of particular examination energy wavelengths, in which the sensor body has an electrically conductive portion or element associated therewith for contacting the patient. This electrically conductive, member is coupled to the signal ground potential of associated signal-processing apparatus to thereby equalize the electrical potential of the patient surface area to which the sensor is applied with the aforementioned signal ground potential. Preferably, an isolation preamplifier is utilized between the sensor and a microprocessor wherein the examination signals are analyzed, to provide the aforementioned signal ground, but in any event this signal ground is maintained separate from and preferably isolated from the primary ground conductor and potential of the processor and/or of the driver circuitry which provides excitation for the electro-optical components. In a particular preferred embodiment, conductive shielding is used in the sensor for reducing electrical noise from ambient sources, and the aforementioned conductive sensor member is electrically connected to such shielding, for improved results. Also, in a preferred embodiment, this shielding substantially encloses an inner portion of the sensor carrying the electro-optical components, in particular, the light-detector, except for openings in the shielding of a size and shape to fit relatively closely around the detector and thereby provide maximal shielding effects for the detector and their associated electrical conductors.

30 Claims, 7 Drawing Sheets

U.S. PATENT DOCUMENTS

| | | | |
|---|---|---|---|
| 4,013,067 | 3/1977 | Kresse et al. | |
| 4,015,595 | 4/1977 | Benjamin, Jr. | |
| 4,063,551 | 12/1977 | Sweeney | |
| 4,091,803 | 5/1978 | Pinder | 128/2.05 P |
| 4,109,643 | 8/1978 | Bond et al. | |
| 4,163,447 | 8/1979 | Orr | 128/666 |
| 4,223,680 | 9/1980 | Jobsis | 128/633 |
| 4,249,540 | 2/1981 | Koyama et al. | 128/666 |
| 4,259,963 | 4/1981 | Huch | 128/635 |
| 4,267,844 | 5/1981 | Yamanishi | 128/633 |
| 4,281,645 | 8/1981 | Jobsis | 128/633 |
| 4,321,930 | 3/1982 | Jobsis et al. | 128/633 |
| 4,332,258 | 6/1982 | Arai et al. | 128/666 |
| 4,336,809 | 6/1982 | Clark | 128/665 |
| 4,344,438 | 8/1982 | Schultz | 128/634 |
| 4,350,163 | 9/1982 | Ford, Jr. et al. | 128/633 |
| 4,380,240 | 4/1983 | Jobsis et al. | 128/633 |
| 4,510,938 | 4/1985 | Jobsis et al. | 128/633 |
| 4,515,165 | 5/1985 | Carroll | 128/664 |
| 4,570,638 | 2/1986 | Stoddart et al. | 128/665 |
| 4,685,464 | 8/1987 | Goldberger et al. | 128/633 |
| 4,763,660 | 8/1988 | Kroll et al. | 128/640 |
| 4,770,179 | 9/1988 | New, Jr. et al. | 128/633 |
| 4,805,623 | 2/1989 | Jobsis | 128/633 |
| 4,819,752 | 4/1989 | Zelin | 128/633 |
| 4,825,872 | 5/1989 | Tan et al. | 128/633 |
| 4,825,879 | 5/1989 | Tan et al. | 128/633 |
| 4,830,014 | 5/1989 | Goodman et al. | 128/665 |
| 4,840,179 | 6/1989 | Ullrich | 128/633 |
| 4,865,038 | 9/1989 | Rich et al. | 128/633 |
| 4,867,557 | 9/1989 | Takatami et al. | 356/41 |
| 4,880,304 | 11/1989 | Jaeb et al. | 356/41 |
| 4,928,691 | 5/1990 | Nicolson et al. | 128/633 |
| 4,938,218 | 7/1990 | Goodman et al. | 128/633 |
| 4,964,408 | 10/1990 | Hink et al. | 128/633 |
| 5,057,695 | 10/1991 | Hirao et al. | 250/575 |
| 5,080,098 | 1/1992 | Willett | 128/633 |
| 5,094,240 | 3/1992 | Muz | 128/633 |
| 5,099,842 | 3/1992 | Mannheimer et al. | 128/633 |
| 5,111,817 | 5/1992 | Clark et al. | 128/633 |
| 5,139,025 | 8/1992 | Lewis et al. | 128/665 |
| 5,140,989 | 8/1992 | Lewis et al. | 128/633 |
| 5,188,108 | 2/1993 | Secker | 128/633 |
| 5,209,230 | 5/1993 | Swedlow et al. | 128/633 |
| 5,217,013 | 6/1993 | Lewis et al. | 128/633 |
| 5,226,417 | 7/1993 | Swedlow et al. | 128/633 |
| 5,299,572 | 4/1994 | Chen et al. | 128/639 |

SPECIALLY GROUNDED SENSOR FOR CLINICAL SPECTROPHOTOMETRIC PROCEDURES

REFERENCE TO RELATED PATENTS AND APPLICATIONS

The general subject matter and environment of the present invention is related to prior application Ser. No. 07/711,452 (filed Jun. 6, 1991), now U.S. Pat. No. 5,217,013, Ser. No. 08/060,853 (now abandoned) and its Continuation application Ser. No. 08/237,321 (filed May 3, 1994) and Ser. No. 08/065,140 (filed May 20, 1993), which are commonly owned with the present invention. Also, but to a lesser extent, the present invention is related to copending application Ser. No. 08/006,705 (filed Jan. 22, 1993), and its prior related applications, as well as Ser. No. 08/069,096, (filed May 28, 1993), all of which are expressly incorporated herein by reference as fully as though set forth in their entirety. More particularly, the present application comprises a Continuation-In-Part of the aforementioned copending application Ser. No. 08/237,321.

This invention relates generally to spectrometry methods and apparatus, and more particularly spectrophotometry; more particularly, the invention relates to biomedical or clinical applications of such technology, as exemplified by electro-optically-implemented non-invasive oximeters, especially cerebral oximeters used in human patient applications. More particularly considered, the invention relates to methods and apparatus for improving the signal quality, and hence the operational accuracy, of clinical biomedical spectrophotometric apparatus such as oximeters, in which wavelength-specific light is applied to a test subject at one point and resultant light intensity is detected at another such point after passing through a given volume of the test subject tissue and/or other biological substance within the particular such volume involved.

BACKGROUND

Noninvasive devices for determining arterial blood oxygen saturation by using spectrophotometric procedures have been known and used for some time, and many different examples of such devices are commonly available and used in medical facilities such as hospitals and the like. Further, a noninvasive cerebral oximeter based on spectrophotometric technology, for noninvasively determining blood oxygen saturation levels on a regional basis within the brain has been developed heretofore by Somanetics Corporation of Troy, Mich., owner of the present invention. In the most basic sense, these devices all operate by introducing light of two or more selected wavelengths at a predetermined location on the patient and measuring the intensity of resulting light at one or more other reasonably close points, and then subjecting the detected intensity signals to extensive comparative analysis by digital computer based on the known differences of absorption between reduced and oxygenated hemoglobin for the different selected wavelengths of light which have been introduced.

In such apparatus, the sources of the selected light spectra introduced into the patient and the detectors for determining resultant intensities are typically implemented by use of light-emitting diodes ("LEDs") and photodiodes, which are mounted in a carrier device of one type or another, the resulting device typically being referred to as a "sensor". In the case of most arterial oximeters, such sensors are either flexible or somehow articulatable, so that they can wrap or otherwise extend around a given portion of the anatomy (e.g., finger, earlobe, etc.), to thereby locate the detector opposite the light source. In the case of the cerebral oximeter, however, the sensor is typically applied to the forehead of the patient, with the light source and detectors disposed laterally adjacent one another so that the light travels through the skin and underlying bone (skull), enters the brain, and is reflected back toward the detectors after traveling through the intervening brain tissue, and back out through the skull, skin, etc.

Accordingly, there are a number of significant differences between the conditions encountered in cerebral oximetry and those encountered in arterial oximetry, particularly in view of the fact that the separation distances between the light sources and detectors must of necessity be substantially greater in cerebral oximetry than in arterial oximetry, since this distance is directly related to the effective depth which the interrogating light spectra travel through the patient and, in order to access (traverse) brain tissue rather than mere boundary layers of skin, bone, etc., this distance is substantially greater in cerebral oximetry than it is in arterial oximetry. Each increment of distance between the source LEDs and detectors significantly reduces the light intensity available at the detectors, however, and in fact it has been found that each centimeter of such spacing causes resultant light intensities at the detectors to be attenuated by a factor of ten. As a result of the necessarily greater separation distances required in cerebral oximeters, the detected light intensities are very small, and they produce detector outputs which are on the order of picoamps. In comparison to typical arterial oximeters, the detector output signals in cerebral oximeters can be of an order of magnitude which is perhaps one hundred times less.

These very small detector outputs encountered in cerebral oximetry therefore create far greater problems with respect to accurate analysis than is true of arterial oximeters, in particular pulse oximeters; in fact, the detector output signals can be so small in cerebral oximeters that they are sometimes lost in the electrical noise that is inherently present in such apparatus, particularly in the operating environment and the many different specific patient conditions encountered. Of course, when this condition exists, it is impossible to calculate any meaningful oxygen saturation values, and even where this is only partially true the accuracy of any values so produced will inherently be highly suspect. In this regard, typical patient environments where cerebral oximeters are most necessary include trauma centers and operating rooms, and it has been found that these environments usually include equipment that produces extensive amounts of electro-magnetic interference (EMI) and/or radio frequency interference (RFI). For example, electrocautery equipment typically used in operating room environments products extensive RFI, and does so at a location very near the oximeter sensor. While various filtering techniques can be utilized in an effort to reduce the effects of such noise, the problem encountered is extremely difficult to even deal with effectively, and essentially impossible to overcome, by using such measures.

SUMMARY OF THE INVENTION

The present invention recognizes certain basic attributes of the problem referred to in the preceding paragraphs, and provides methods and apparatus for essentially overcoming the same in an effective, relatively simple, and economically advantageous manner, by which spectrophotometric oximeter signal-to-noise ratio is improved by a factor of on the order of ten times.

More particularly, the invention recognizes that the operating room noise referred to above is or can be conducted through a patient and actually detected by the sensor, and that in a particular sense this noise can be effectively eliminated or substantially reduced by in effect establishing an electrical path between the patient and a portion of the oximeter control and actuation apparatus, so that the surface potential of the patient is directly linked (tied) to a reference potential having a known and predetermined value, while at the same time isolating and insulating the patient from all other excitation levels and conductive paths communicating with the oximetry apparatus.

Accordingly, in accordance with the invention, a novel concept is provided along with preferred implementations of such concept, by which the signal-to-noise ratio present in the photodetector outputs which are fed back for analysis are very substantially and significantly improved, by orders of magnitude, in a simple and effective manner.

More particularly considered, the invention provides an oximeter sensor structure which provides an effective conductivity path directly from the patient-contacting surface back to a predetermined point in the detector output signal-conducting path, in particular, the floating ground established in the detector circuitry. Most effectively this is done by actually making the sensor body conductive in at least the area immediately adjacent the detectors, so that the related surface area on the patient reflects this controlled potential and any such noise otherwise present is conducted away without contaminating the detector output. Other types of conductive members could also be utilized in accordance with the invention, including a separate electrode incorporated in a strap or the like for example.

In addition to the foregoing, the invention provides novel and effective implementations for signal-conducting path referred to above, which cooperate with the sensor configuration in providing the substantial noise reduction and improved signal level noted, while at the same time providing greater safety for the patient by increased isolation of other electrical circuits and componentry.

The foregoing principal objectives and advantages of the invention, together with other such objectives and advantages, will become more apparent after consideration of the ensuing description of preferred embodiments taken in view of the appended drawings.

INFORMATION FROM RELATED APPLICATIONS AND PRIOR ART

Figure 1:
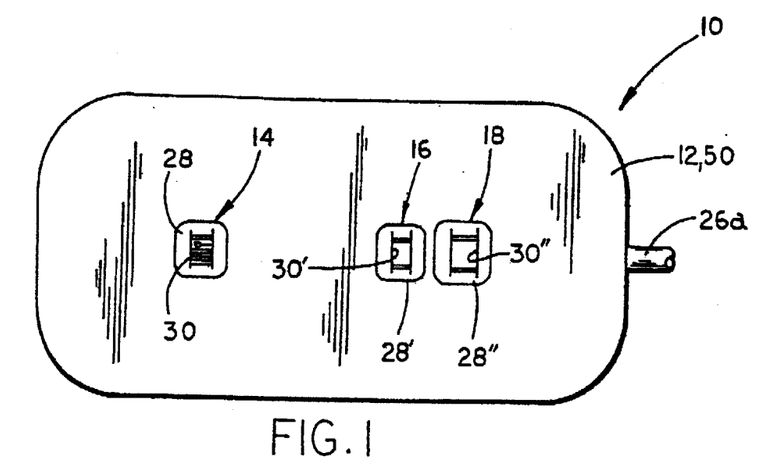
FIGS. 1 and 2 are top and sectional side elevational views, respectively, taken from the above-referenced copending application Ser. No. 08/273,366, showing the basic overall structure of a preferred form of sensor for a cerebral oximeter, exemplifying the environment of present invention as well as a preferred implementation thereof.
Figure 2:
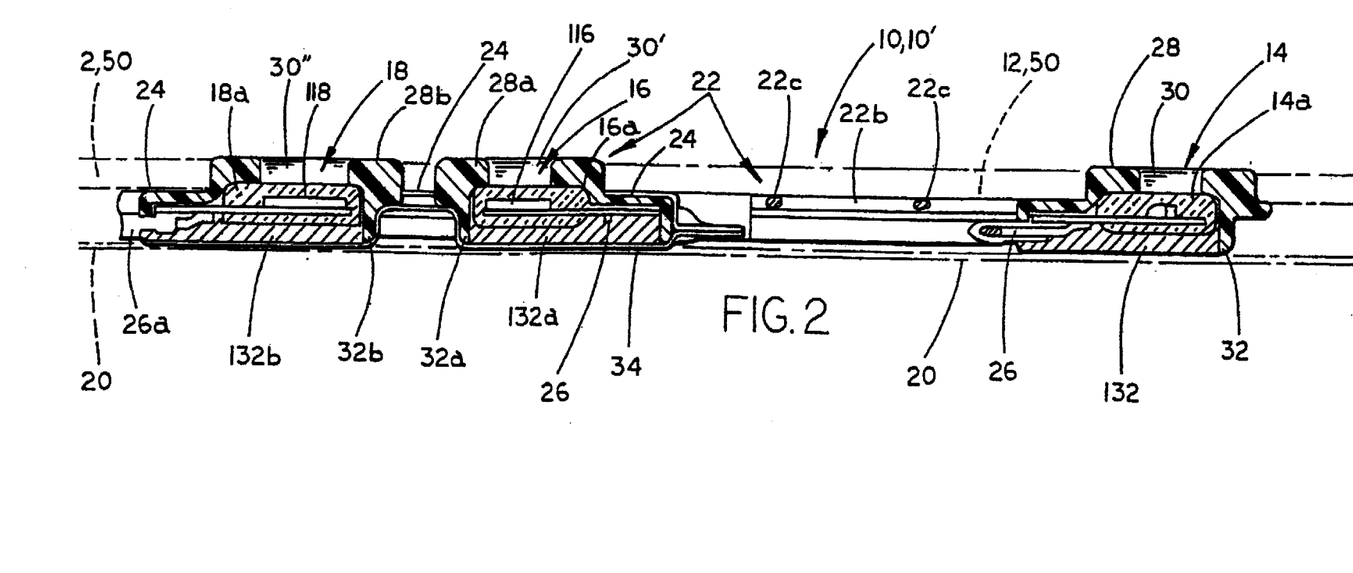

As indicated above, related and commonly-owned application Ser. Nos. 08/060,853 and 08/065,140 (and its continuation application Ser. No. 08/273,366) illustrate and describe the structure and operating environment of "sensor" devices for use in optical cerebral oximeters such as that toward which the present invention is particularly directed, notwithstanding its broader aspects and more extensive potential applications, and FIGS. 1 and 2 are taken directly from the latter such application, with the same numbering retained. While these prior related applications are incorporated herein by reference as fully as though set forth herein and therefore need not be specifically repeated, it is pointed out for convenience that in the sensor 10 of FIGS. 1 and 2, the light sources (grouped LEDs) are designated generally by the numeral 14, the "near" and "far" detectors of the preferred oximeter embodiment are designated 16 and 18, respectively, and the interconnecting electrical conductors communicating between sensor 10 and the oximeter apparatus via a shielded cable 26A. Of particular relevance to the present application is a softly resilient outer patient-contacting pad or cover 12, which in these prior applications is implemented by use of the open-celled polymeric foam material known as "Poron". The outermost side of the pad or cover is coated with a suitable medical-grade adhesive, by which the sensor is securely but temporarily attached to the forehead of the patient during use. As disclosed in these related prior applications, a preferred such adhesive is a medical grade acrylic transfer adhesive made by Minnesota Mining and Manufacturing Company ("3M"). It is important to note that, in this prior implementation, both the outer pad 12 and its adhesive coating are non-conductive electrically, since prior thinking and accepted practices were to make every effort to insulate the patient from direct contact with any electrically-conductive element, to thereby avoid any inadvertent contact with electricity.

DESCRIPTION OF PREFERRED EMBODIMENTS

Figure 3:
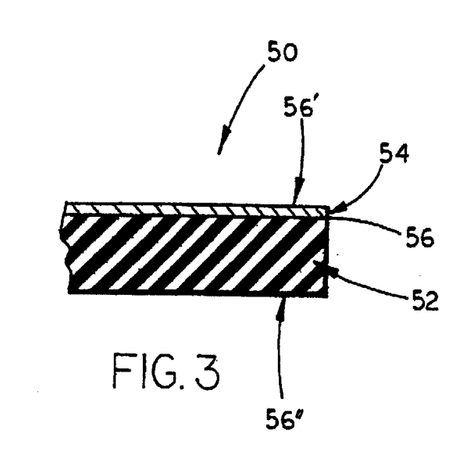
FIG. 3 is an enlarged fragmentary sectional side elevation depicting a preferred embodiment of the outer layers of a sensor in accordance with the invention.

While the overall structure of the sensor 10' in accordance with the present invention is preferably the same in most respects as that illustrated in FIGS. 1 and 2 (and described in the referenced and incorporated copending application Ser. No. 08/273,366), a marked difference exists in the nature of the outer pad 12, which is illustrated in FIG. 3 and designated herein by the numeral 50. In this respect, the non-conductive outer pad 12 of the prior embodiment described in the related application identified above and its non-conductive adhesive coating are replaced by a composite structure comprised of electrically conductive elements. Thus, the outer pad or cover 50 of the present invention (which is to replace the pad 12 of the prior embodiment) preferably comprises a layer 52 of resilient material of an electrically conductive nature, for example conductive neoprene rubber, and an adjacent layer of copper tape 54 adhesively secured thereto. Each side of resilient layer 52 is coated with a thin layer of conductive adhesive 56, whereby the outermost such layer (designated 56'), which contacts the patient, will securely affix the entire sensor thereto, while the innermost such layer (designated 56"), which contacts the other part of the sensor body and in particular the shielding material (designated by the numeral 24 in FIGS. 1 and 2 and essentially surrounding the detectors 16 and 18 except for their light-passage openings) will securely fasten the pad or cover 50 thereto in a completely conductive manner. Accordingly, a direct connective path is established from the forehead of the patient to the control and actuating circuitry of the oximeter (depicted generally in FIG. 4 and described hereinafter) through cable 26A.

In accordance with the invention as presently contemplated, the conductive neoprene layer 52 preferably comprises commercially available conductive Polychloroprene having a durometer of about 65 (plus or minus 5), Shore A (RDI formula #RD136A). The "copper tape" layer 54 preferably comprises the product known as "Flexshield 8016" sold by Adhesives Research, Inc. of Glen Rock, Pa., which combines a copper-impregnated tip-stop nylon material (available from Monsanto Company and designated as "Flectron") with a homogeneously conductive adhesive sold by Adhesives Research, Inc. under the designation "EC-2". The conductive adhesive 56 preferably comprises the product sold by Adhesives Research, Inc. under the trademark "ARclad 8006", which comprises an unsupported, self-wound transfer adhesive featuring the aforementioned "EC-2" pressure-sensitive conductive adhesive. No doubt, other such materials and other particular structural layups or arrangements may also be utilized, but these particular materials and the particular structure described comprise the most preferred embodiment and best mode presently contemplated.

With respect to the selected materials and components of the pad 50, it is important that conductivity be relatively high in a lengthwise direction (Z axis), as well as through their thickness. The conductive layer 54 is principally included to enhance (increase) conductivity between the patient and the other components, and particularly to make the entire relevant sensor area an effective conductor. In this regard, the preferred components (materials) noted above exhibit excellent adhesion qualities and conductivity; for example, the preferred adhesive 56 has a volume resistance of less than five ohms per square inch and a surface resistance of approximately 30K ohms per square centimeter, with fast static dissipation and a low Z-axis resistance. Similarly, the conductive layer 54 incorporates a very favorable adhesion characteristic and excellent conductivity while at the same time providing additional and significant shielding properties (more than 102 db at 100 KHz), while at the same time being highly flexible and readily conformable to adjacent surfaces. Examples of preferred thicknesses of these components are, for layer 52, 0.034 inch, plus or minus 0.012, for the "copper tape" layer 54, approximately 0.004 inch, and for the conductive adhesive layers 56, approximately 0.001 inch. As will be understood, a releasable liner (not specifically shown) should be used on the outside of layer 56' to facilitate handling of the pad and sensor, such liner being removed just prior to use of the sensor. It is to be noted that in addition to the qualities indicated above, the materials just identified provide desirably low or negligible primary skin irritation and sensitization, and the preferred adhesive passes FDA cytotoxicity testing.

Figure 4:
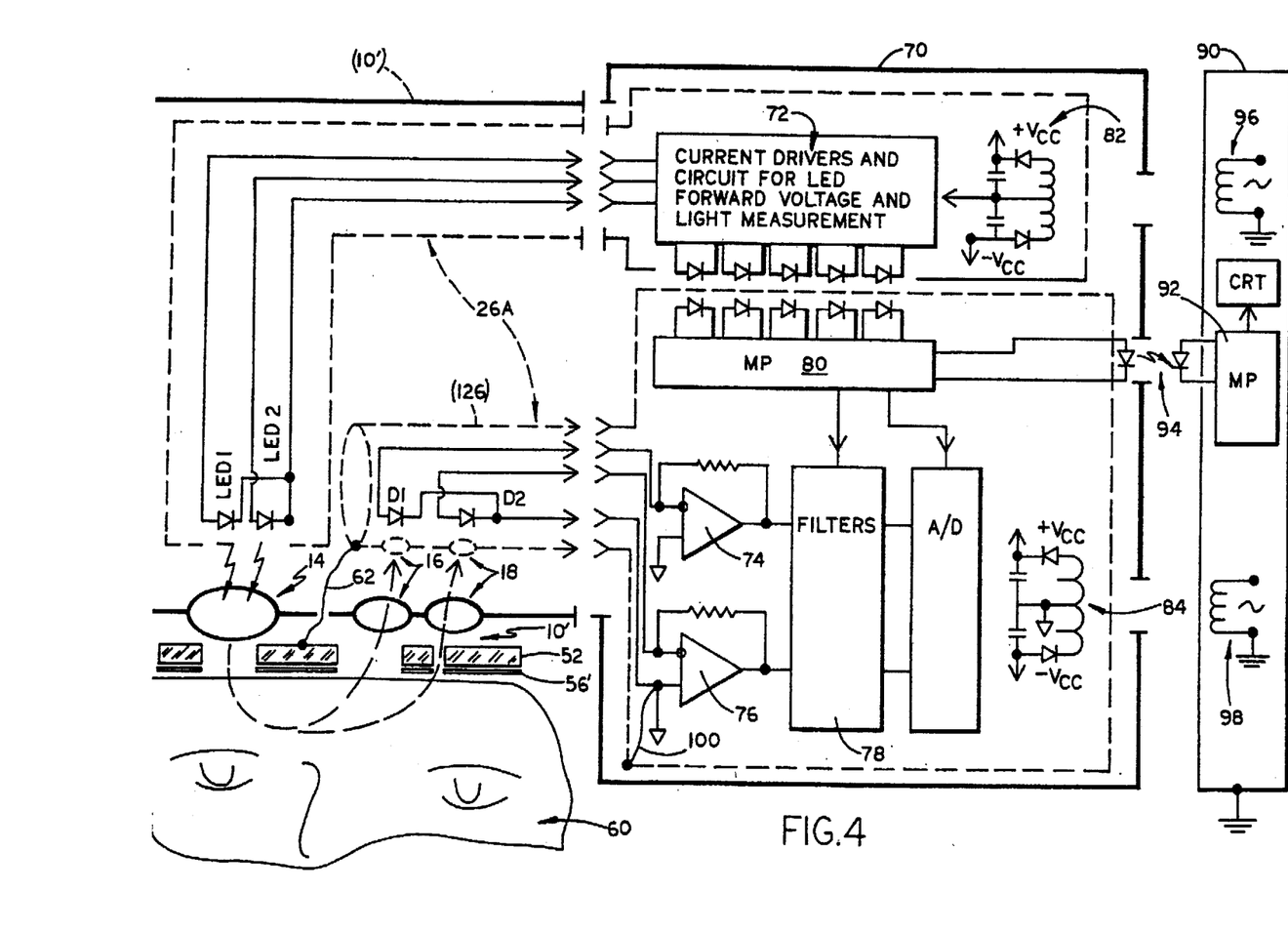
FIG. 4 is a fragmentary, pictorialized schematic representation depicting the application of the sensor to the test subject and presenting a block diagram of the related electrical circuitry.
Figure 4A:
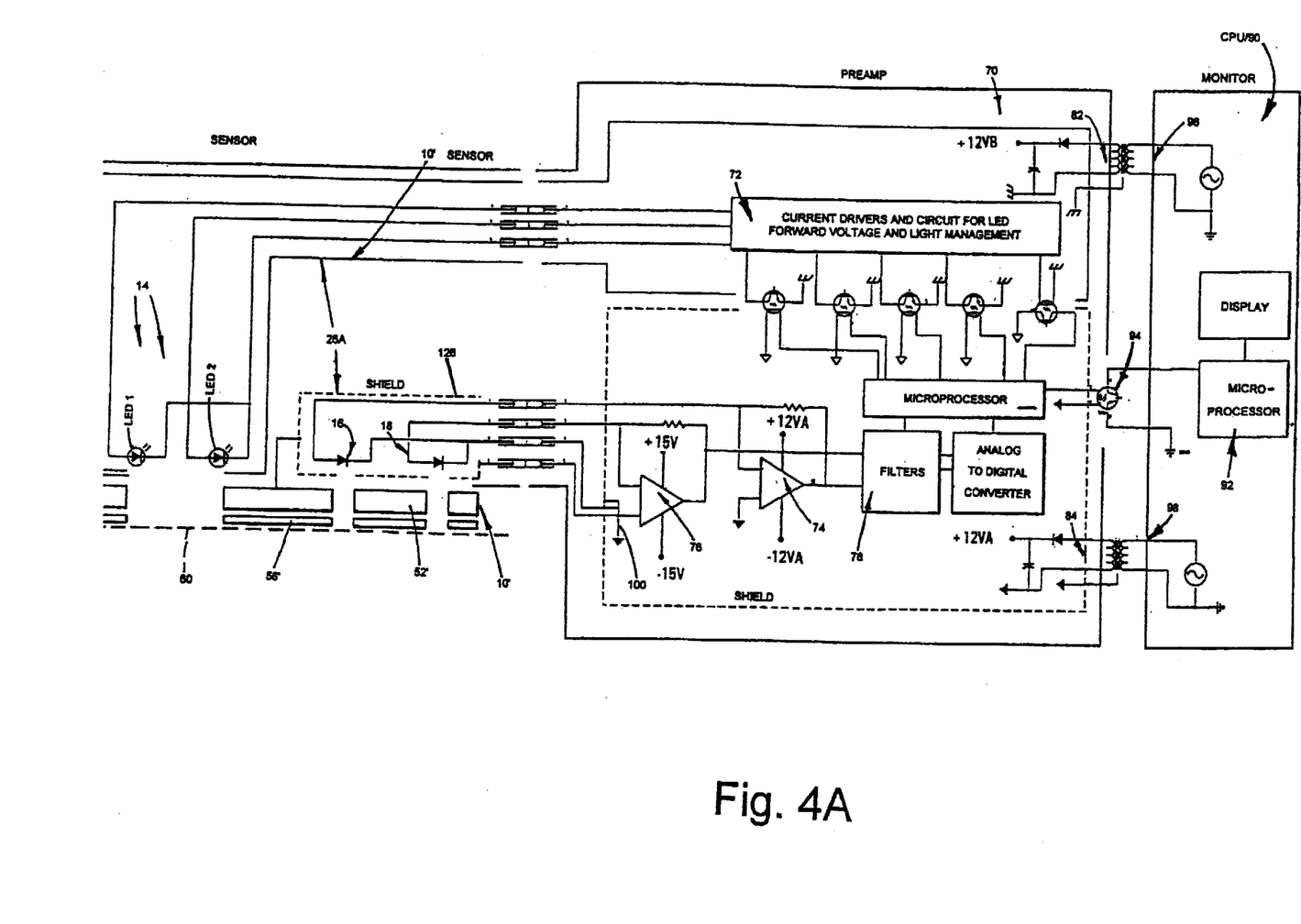
FIG. 4A is a counterpart of FIG. 4, drawn by use of a more formal convention.

While the basic structure and use of the sensor 10' in accordance with the present invention is consistent with that described in the related copending applications referenced above and incorporated herein by reference, the general arrangement and particular new aspects thereof are illustrated in FIG. 4. As seen there, the new type of sensor 10' incorporating the conductive patient interface pad or cover 50 is secured directly to the forehead of the patient 60 by the outermost adhesive layer 56' and, as indicated above, the sensor 10' is electrically coupled by the cable 26A back to the control and actuation components of the oximeter itself, designated in FIG. 4 as the "CPU/Monitor" 90, with an in-line preamp 70. In this general connection, it will be noted that FIG. 4 symbolically illustrates the direct electrical connection between the elastomeric layer 52 and the shielding componentry 24 of sensor 10' and cable 26A by a physical conductor 62, although in fact this conductor comprises the conductive layers themselves, including the adhesive layers 56.

While the general nature and operation of the oximeter itself is described in the various copending and incorporated applications, and the general nature and the components of the preamp 70 and "CPU/Monitor" 90 will be readily understood by those skilled in the art, especially in light of the incorporated disclosures, particular attributes of these are briefly commented upon here. In this regard, it is particularly pointed out that the "CPU/Monitor" 90 is effectively isolated from the preamp 70, and that the light source 14 (LED1 and LED2) its associated current drivers etc. 72 is isolated from the detectors 16 and 18, (comprising the photodiodes D1 and D2 and interconnected circuitry, including amplifiers 74, 76, filters 78, etc.) Further, the microprocessor 80 incorporated in preamp 70 is coupled to its operationally-related microprocessor 92 of the central processing unit 90 by an optical pair 94, thereby avoiding all conductive paths which otherwise would exist therebetween.

In addition, it should be noted that the current drivers etc. 72 of preamp 70 have their own separate power supply transformer winding 82, and the same is true of the detector circuit, which has its own supply transformer winding 84, preamp supply transformer 82 being inductively coupled to a corresponding separate primary winding 96 of the CPU 90, and detector supply transformer 84 being inductively coupled to a separate CPU primary winding 98. It will be recognized that the arrangement just described provides essentially complete isolation of the different major components and operational component groupings from one another. In this arrangement, the patient 60 is effectively directly coupled to sensor 10' and the conductive path 62 to the shielding 24 and cable 26A, and the latter is directly coupled to the signal ground of the detector network (but isolated from, the power ground of the light source and electrical supplies). Thus, the patient 60 is in effect maintained at the same electrical potential as the signal ground of the detector circuitry in preamp 70, which is a floating ground not equatable with the earth ground of the power circuitry. In this manner, the extensive environmental noise of operating rooms, trauma centers, etc., as referred to above, is effectively eliminated or at least very substantially reduced, with results which are graphically illustrated in FIGS. 5-8 inclusively.

Figure 5:
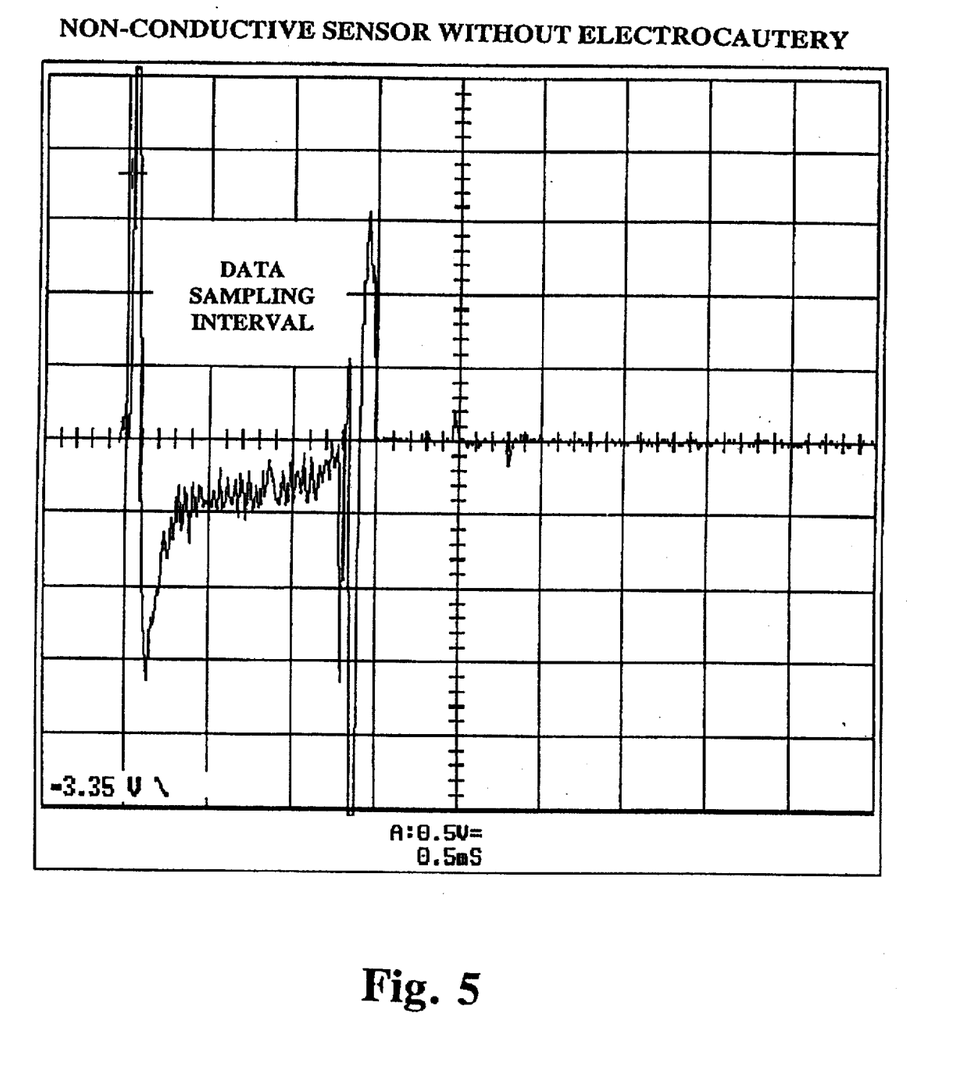
FIGS. 5-8 are graphical representations of the detector output wave shapes under various conditions, as labeled, illustrating the actual operational conditions involved in practice of the invention.
Figure 6:
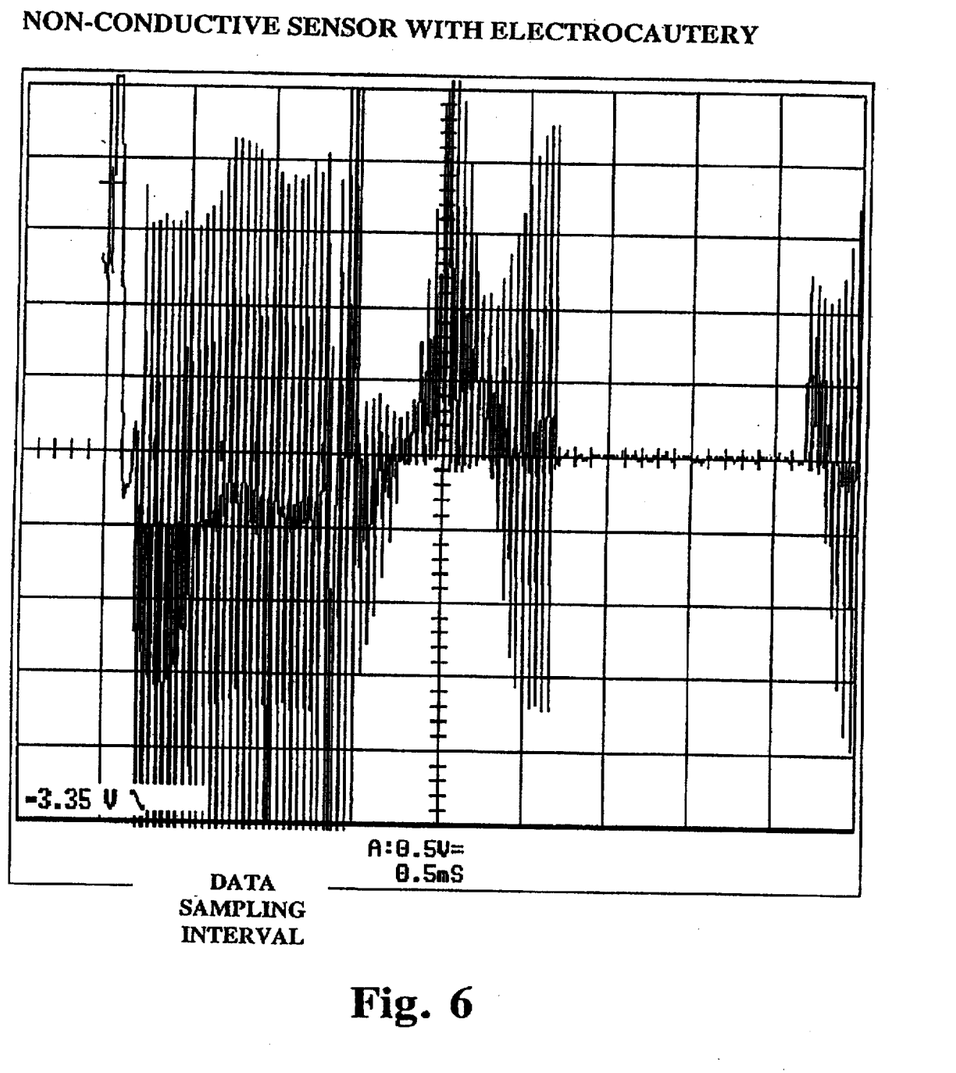

With more particular reference to FIGS. 5-8 each such graph constitutes a closely representative depiction of the amplified output of the photodiodes D1 and D2 comprising detectors 16 and 18, i.e. the output of amplifiers 74 and 76 (FIG. 4), taken during a time span which includes a particular data sampling interval (as designated) which, it should be noted, is longer in duration than the actual period during which source LED1 and LED2 are pulsed. Further, each different FIG. 5-8 inclusive represents a particular set of conditions, as labeled. Thus, FIG. 5 represents a "nonconductive sensor" such as that taught in incorporated copending application Ser. Nos. 08/065,140 and 08/273,366 and depicted in FIGS. 1 and 2, operating without an electrocautery noise source (all such graphical figures having the same coordinates in magnitudes, as labeled, i.e., the ordinate units representing 0.5 volts and the abscissa representing 0.5 milliseconds). As illustrated in FIG. 5, under these conditions the signal output 110 constitutes a relatively noisy but reasonably distinctive pulse which starts from a spike of about 1.5 v. and declines toward zero, with an average magnitude of perhaps 0.3/0.4 v. This graphical representation should be compared to that of FIG. 6, depicting the corresponding output from the same sensor configuration during a time when the electrocautery noise source is in operation. The nature and extent of the differences are clearly self-evident; i.e., the burst of FIG. 6 has extensive noise effects which in essence obscure the data signal and which would clearly make analysis difficult at best.

Figure 7:
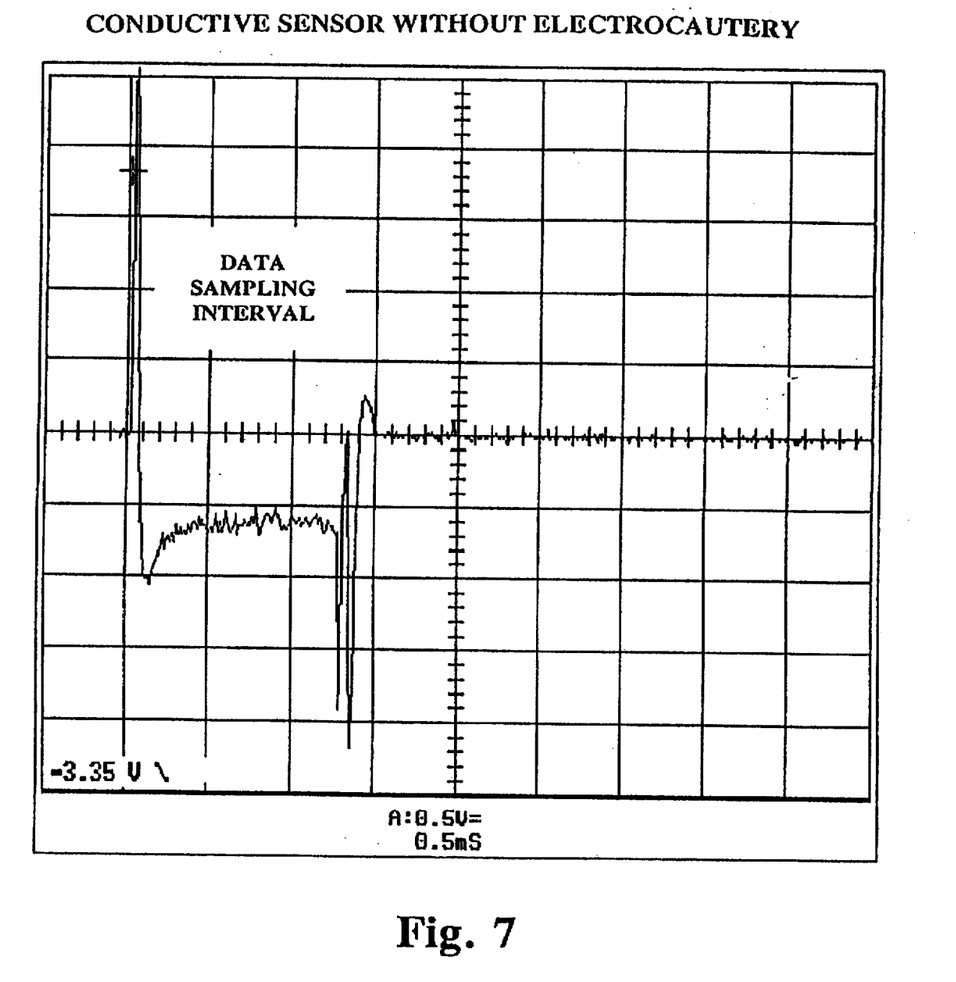
Figure 8:
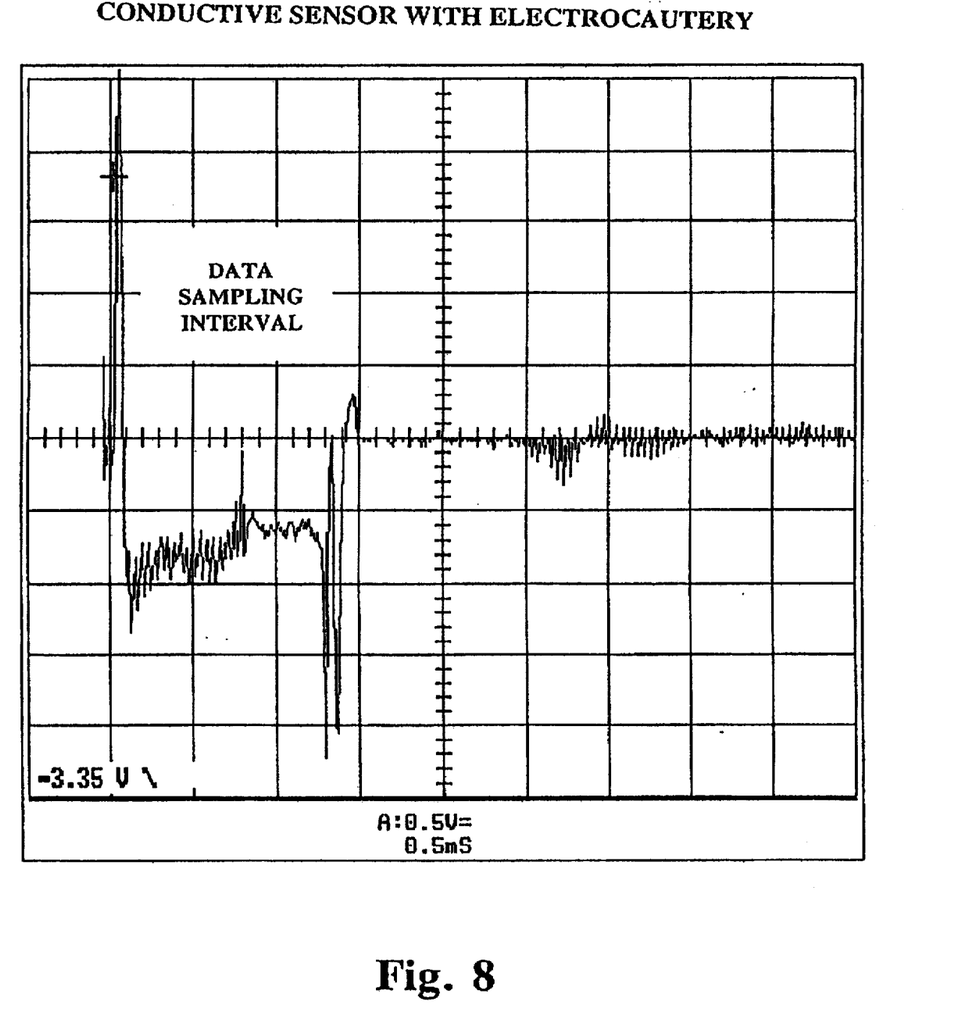

In contrast to the showings of FIG. 5 and FIG. 6, FIGS. 7 and 8 show the very different results obtained under the same circumstances with a conductive sensor 10' incorporating a conductive pad 50 in accordance with the present invention. As there shown, the detector output signal burst 220, 220' is much cleaner and well-defined, with minimal noise content. In fact, the burst 220' of FIG. 8, taken with an electrocautery knife in operation, is actually cleaner than the burst 110 of FIG. 5, which was taken without the electrocautery in operation. Furthermore, the bursts 220 and 220' of FIGS. 7 and 8 are very similar to each other, i.e., the presence or absence of electrocautery operation making little difference.

The graphical representations of results provided in FIGS. 5–8 inclusive are in fact representative, and certainly not idealized. In actual testing, the results provided by the invention are shown to improve the detector output signal-to- noise ratio by a factor of about 10 times. As will be readily understood, the significance of this improvement is both surprising and highly meaningful, clearly evidencing a very substantial improvement in operating accuracy which is of utmost importance to the overall performance, accuracy and acceptability of the oximeter itself.

It is to be pointed out that the improvement referred to above, while resulting in large part from the conductive path extending from the surface of the test subject (patient) to the preamp 70 by the conductive sensor 10', this implementation and result is itself enabled and substantially enhanced by the provision of the isolated preamp implementation shown and described in FIG. 4, since it would not be acceptable or advisable to merely connect the patient to a non-isolated path or ground conductor, especially not the earth ground used in the power circuitry. Additional benefits are also obtained by this isolation, in the form of improved accuracy and reduced noise, distortion, etc. With this point in mind, however, it should be appreciated that there are or may be entirely viable alternative measures for implementing the underlying concept, i.e., in addition to or instead of the conductive sensor implementation shown and described, and this concept should be born in mind in considering the scope of this patent and its appended claims.

It is to be pointed out once again that while the foregoing disclosure addresses a particular preferred embodiment, and best mode, the particular apparatus described and the various detailed aspects thereof noted are regarded as pertaining to only the most preferred version of the invention and to merely illustrate the principles and concepts involved in the invention, other embodiments and versions of the invention no doubt being feasible and potentially appropriate in other circumstances. It is therefore to be understood that the foregoing description of a particular preferred embodiment is provided for purposes of description and illustration, and not as a measure of the invention, whose scope is to be defined solely by reference to the ensuing claims. Embodiments of the invention differing from those set forth above which nonetheless utilize the underlying concepts of the invention and incorporate its spirit should therefore be considered as within the scope of the claims appended below, unless such claims by their language specifically state otherwise.

The embodiments of the invention in which an exclusive property or privilege is claimed are defined as follows:

1. An improved sensor apparatus for use in conducting clinical patient examinations by spectrometric apparatus wherein a sensor carrying electrically actuated spectrometric signal-generating components is placed in contact with a predetermined area of the patient for transmittal of selected energy wavelengths therebetween and at least some of said components are electrically coupled to signal-processing circuits of an electrically powered processor which also includes power circuits distinct from said signal-processing circuits, to transmit electrical examination signals to said processor for processing, comprising:

a sensor body carrying electrically actuated components used in said transmittal of energy wavelengths and said examination signals;

said sensor body further having an electrically conductive surface portion for contacting said patient, an electrically conductive path extending from said surface portion, and an externally accessible electrical contact connected to said conductive path, whereby the electrical potential of said patient at the area contacted by said sensor may be accessed;

means for electrically coupling at least some of said electrically actuated components to said signal-processing circuits of said processor to convey said electrical examination signals thereto; and means for electrically coupling said externally accessible electrical contact to certain of said signal-processing circuits of said processor in a manner maintaining electrical separation of said conductive surface portion of said sensor from said power circuits of said processor in said transmittal of energy wavelengths and said examination signals, to thereby establish and maintain substantially the same electrical potential between said area of said patient and said certain signal-processing circuits and thereby substantially reduce the electrical noise content of examination signals transmitted to said circuits.

2. The improved sensor apparatus according to claim 1, further including electrical circuitry and components for electrically isolating said conductive surface portion of said sensor body from the electrical power circuits of said processor which receives examination signals from said sensor.

3. The improved sensor apparatus according to claim 1, wherein said signal-processing circuits include a signal ground distinct from said power circuits and including electrical circuitry for electrically coupling said externally accessible contact to said signal ground to thereby establish and maintain substantially the same electrical potential therebetween and thereby substantially reduce the electrical noise content of examination signals transmitted to said processor.

4. An improved sensor for use in conducting clinical patient examinations by spectrophotometric apparatus wherein a sensor is placed in contact with the patient for transmittal of selected light energy wavelength signals therebetween and resulting examination signals are coupled to a processor for processing, comprising:

a sensor body having a support structure for mounting mutually distinct and separately operable spectrophotometric light-producing and light-receiving components used in said transmittal of energy wavelength signals and said examination signals, and a plurality of said mutually distinct components carried on said support structure;

said sensor body further having a compliant outer layer carried by said support structure for conformably contacting said patient;

said sensor body further having an electrically conductive portion associated with said compliant outer layer and positioned for direct contact with said patient during transmittal of said light energy signals to provide an electrode for accessing the electrical potential of said patient at the location of said direct contact.

5. The improved sensor of claim 4, wherein said outer layer comprises a yieldable material and said conductive portion comprises at least a portion of said yieldable material.

6. The improved sensor of claim 5, wherein at least portions of said yieldable material are electrically conductive.

7. The improved sensor of claim 6, wherein said yieldable material comprises a polymeric base which includes electrically conductive elements.

8. The improved sensor of claim 6, further including electrically conductive adhesive on at least one side of said outer layer.

9. The improved sensor of claim 4, further including circuitry and components for coupling said electrically conductive portion of said sensor body to predetermined electrical circuit portions of a processor while maintaining electrical isolation between said conductive portion of said sensor body and at least said predetermined electrical circuit portions of said processor.

10. The improved sensor of claim 9, wherein said circuitry and components include an isolation preamp having isolated power and signal-processing paths.

11. The improved sensor of claim 4, wherein said sensor body includes an electrically conductive layer disposed beneath said compliant outer layer to provide a means for shielding ambient sources of electrical noise, and wherein said conductive layer is electrically connected to said electrically conductive portion providing said electrode.

12. The improved sensor of claim 11, wherein at least portions of said compliant outer layer are electrically conductive and are connected to said electrically conductive layer which provides said means for shielding.

13. The improved sensor of claim 11, wherein said compliant outer layer comprises an electrically conductive yieldable polymeric member.

14. The improved sensor of claim 13, wherein said electrically conductive layer which provides said means for shielding comprises a thin metal sheet disposed in contact with said yieldable polymeric member.

15. The improved sensor of claim 14, wherein said thin metal sheet has apertures formed therein which fit generally around the edges of and window at least one of said spectrophotometric light-receiving components while shielding such component and its connected electrical conductors from ambient sources of electrical noise.

16. The improved sensor of claim 15, wherein said thin metal sheet wraps around and generally envelopes said at least one of said spectrophotometric light-receiving components.

17. An improved sensor apparatus for use in conducting clinical patient examinations by spectrometric procedures in which selected energy wavelength signals are transmitted to the patient and resulting examination signals are received and coupled to an electrically powered processor for processing to obtain predetermined clinical patient data, said apparatus comprising:

a sensor for contacting said patient and transmitting said energy wavelength signals thereto, said sensor including a body having electrical components used in said transmittal of energy wavelength signals and said receipt of examination signals;

means for electrically coupling said sensor electrical components to processing circuits of said processor, for transmittal and receipt of said energy signals and said examination signals therebetween;

an electrically conductive member associated with said sensor for contacting said patient at a predetermined location, and an electrically conductive path adapted to connect said conductive member to said processor, whereby the electrical potential of said patient in the location contacted by said conductive member may be accessed;

said processor having electrical power circuits and at least one ground potential conductor; and means for electrically isolating said conductive member from the electrical power circuits of said processor including the ground potential conductors thereof, and for establishing and maintaining substantially the same electrical potential between said member and at least portions of said processing circuits to thereby substantially reduce the electrical noise content of said examination signals when transmitted to said processor.

18. The improved sensor apparatus recited in claim 17, wherein said electrically conductive member comprises an integral part of said sensor.

19. The improved sensor apparatus recited in claim 18, wherein said electrically conductive member comprises part of said sensor body.

20. The improved sensor apparatus recited in claim 19, wherein said sensor body includes a compliant outer layer for conformably contacting said patient, and said electrically conductive member is carried by said outer layer and positioned for direct contact with said patient.

21. The improved sensor apparatus recited in claim 20, wherein at least portions of said compliant outer layer are electrically conductive and comprise said conductive member.

22. The improved sensor apparatus as recited in claim 21, further including electrically conductive adhesive on at least one side of said outer layer.

23. An optical sensor unit for use as a patient interface device in conducting in vivo spectrophotometric patient examination, comprising in combination:

a thin lightweight body of multilayered construction and generally planar configuration; said body having a longitudinal support member and a light source carried by said support member to emit light of at least two selected wavelengths outwardly from a first side of said body and to introduce such light into the patient through a selected surface area;

at least one electro-optical light detector carried by said support member at a particular spacing from said light source, said at least one detector being oriented toward said first side of said body and adapted to be exposed to the selected patient surface area to receive light therethrough after it has been introduced by said source; electrical conductors carried at least in part by said support member and coupled to said at least one light detector to convey output signals therefrom representative of the resultant light received thereby from said patient, said conductors extending outwardly from said support member for coupling to a remotely located signal-processing device;

said body further including means for shielding said at least one light detector and at least portions of said electrical conductors from ambient sources of electrical noise and/or like distortion, to help maintain the fidelity of said signals to the detected representative light; and said shielding means including at least one thin layer of lightly flexible, electrically conductive sheet metal, said layer overlying at least portions of said longitudinal support member adjacent said at least one detector and being particularly apertured to fit closely around the perimeter of said at least one detector; said at least one detector having light-admitting portions inside said perimeter, and said particularly apertured layer of conductive sheet metal exposing said light-admitting portions while covering substantially all of the immediately adjacent structure including said electrical conductors to which said at least one detector is connected, to thereby provide enhanced shielding from ambient sources of electrical noise.

24. The optical sensor unit as recited in claim 23, wherein said at least one thin sheet-metal layer substantially encloses at least portions of said longitudinal support member disposed in juxtaposition to said detector.

25. The optical sensor unit as recited in claim 23, wherein said at least one thin sheet metal layer is substantially coextensive with and overlies said longitudinal support member throughout the portion thereof on which said at least one detector and connected conductors are located.

26. The optical sensor unit as recited in claim 23, wherein said means for shielding further includes a sheath surrounding at least portions of said conductors extending outwardly from said body, and wherein said at least one thin sheet metal layer is electrically coupled to said sheath.

27. The optical sensor unit as recited in claim 23, wherein said shielding means includes a sheet of conductive foil wrapped about and substantially enveloping portions of said longitudinal support member and the electrical conductors carried thereupon.

28. The optical sensor unit as recited in claim 27, wherein said means for shielding further includes a sheath surrounding at least portions of said conductors, and wherein said foil, said thin sheet metal layer and said sheath are all electrically interconnected.

29. The optical sensor unit as recited in claim 23, wherein said at least one light detector comprises a photodiode which has a sensitivity on the order of about 500 milliamps per watt and is of a low-noise type.

30. The optical sensor unit as recited in claim 23, wherein said light source comprises at least one LED having an output on the order of about three milliwatts and an output light solid angle of about ninety degrees.

\* \* \* \* \*